United States Patent [19]
Fitzpatrick et al.

[11] Patent Number: 5,989,925
[45] Date of Patent: Nov. 23, 1999

[54] ANTIBODY TO AND ASSAY FOR PEPTIDE LINKED-PYRIDINOLINE AS INDICATOR OF BONE RESORPTION LEVEL

[75] Inventors: Judith Fitzpatrick, Tenafly, N.J.; Regina Lenda, Wesley Hills, N.Y.; Zijian Zeng, Warren, N.J.

[73] Assignee: Serex, Inc., Maywood, N.J.

[21] Appl. No.: 08/884,148

[22] Filed: Jun. 27, 1997

[51] Int. Cl.$^6$ .......................... G01N 33/553; C07K 16/81
[52] U.S. Cl. .......................... 436/525; 436/530; 436/815; 530/388.9; 530/389.8; 530/391.1; 530/391.3; 530/809; 935/95; 935/110
[58] Field of Search ................... 435/7.1, 7.93; 436/525, 530, 815; 530/388.9, 389.8, 391.1, 391.3, 809; 935/95, 110

[56] References Cited

U.S. PATENT DOCUMENTS

| | | | |
|---|---|---|---|
| 4,973,666 | 11/1990 | Eyre | 530/323 |
| 5,300,434 | 4/1994 | Eyre | 435/240.2 |
| 5,320,970 | 6/1994 | Eyre | 436/536 |
| 5,527,715 | 6/1996 | Kung et al. | 436/547 |
| 5,620,861 | 4/1997 | Cerelli et al. | 435/7.1 |
| 5,661,039 | 8/1997 | Kung et al. | 436/501 |

OTHER PUBLICATIONS

Bailey, A. J. et al., "Age related changes in the reducible cross–links of collagen," *FEBS Lett.* 16(2):86–88 (1971).

Banes, A. J., et al., "Nonmineralized and Mineralized Compartments of Bone: The Role of Pyridinoline in Nonmineralized Collagen," *Biochem. Biophys. Res. Commun.* 113(3):975–981 (1983).

Barnes, M. J. et al., "Age–Related Variations in Hydroxylation of Lysine and Proline in Collagen," *Biochem. J.* 139(2):461–468 (1974).

Eyre, D. R., "Crosslink Maturation in Bone Collagen," in *The Chemistry and Biology of Mineralized Connective Tissues*, pp. 51–55, (Veis, A. ed.) (Elsevier, New York, 1981).

Eyre, D. R., "Crosslink Maturation in Bone Collagen," *Develop. Biochem.* 22:50–55 (1981).

Eyre, D.R. et al., "Quantitation of Hydroxypyridinium Crosslinks in Collagen by High–Performance Liquid Chromatography," *Analyt. Biochem.* 137:380–388 (1984).

Eyre, D. R. In: *The Chemistry and Biology of Mineralized Tissues*, p. 105, (Butler, W. T. ed.) (Ebsco Media Inc., Birmingham, Ala., 1985).

Eyre, D. R. et al., "Cross–linking in Collagen and Elastin," *Ann. Rev. Biochem.* 53:717–748 (1984).

Fujimoto, D. et al., "Isolation and Characterization of a Fluorescent Material in Bovine Achilles Tendon Collagen," *Biochem. Biophys. Res. Commun.* 76(4):1124–1129 (1977).

Gunja–Smith and Boucek, "Collagen cross–linking compounds in human urine," *Biochem J.* 197(3):759–762 (1981).

Robins, S. P., "An enzyme–linked immunoassay for the collagen cross–link pyridilone," *Biochem J.* 207(3):617–620 (1982).

Robins et al., "Measurement of the cross linking compound, pyridinoline, in urine as an index of collagen degradation in joint disease," *Ann. Rheum. Diseases* 45:969–973 (1986).

Singer, F. R., et al., "Paget's Disease of Bone," in *Metabolic Bone Disease, vol. II*, pp. 489–575, (eds. Avioli, L. V. and Krane, S. M.) (Academic Press, New York, 1978).

Walters, C. et al., "Collagen Crosslinks in Human Dentin: Increasing Content of Hydroxypyridinium Residues with Age," *Calc. Tiss. Intl.* 35:401–405 (1983).

*Primary Examiner*—Mary E. Ceperley
*Attorney, Agent, or Firm*—Arnall Golden & Gregory, LLP

[57] ABSTRACT

A monoclonal antibody, Serex A93, recognizes peptide linked pyridinoline in Type I bone collagen fragments and can be used to quantitate bone resorption. The hybridoma producing this antibody has been deposited with the American Type Culture Collection, Rockville, Md., under accession number HB-12254. The epitope reactive with the antibody is stable to acid hydrolysis and therefore is not a linear peptide. The antibody recognizes pyridinoline in bound or conjugated form, but not in the free form found in urine. The antibody is useful in immunoassays for determining bone resorption, utilizing body fluids such as urine, saliva, blood, or sweat.

16 Claims, 6 Drawing Sheets

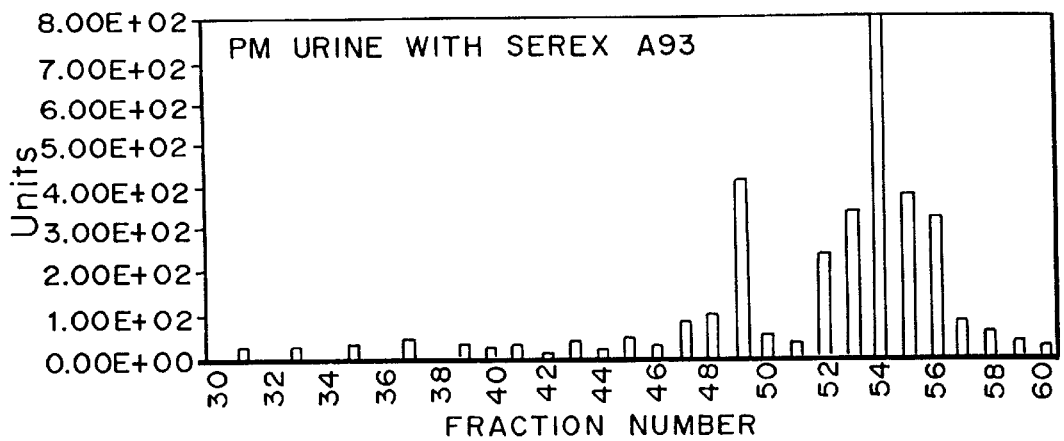
FIG. 1A  POSTMENOPAUSAL (PM) URINE WAS RUN ON A P-10 BIOGEL COLUMN AND EACH FRACTION WAS ANALYZED BY ALL THE AVAILABLE ASSAYS.
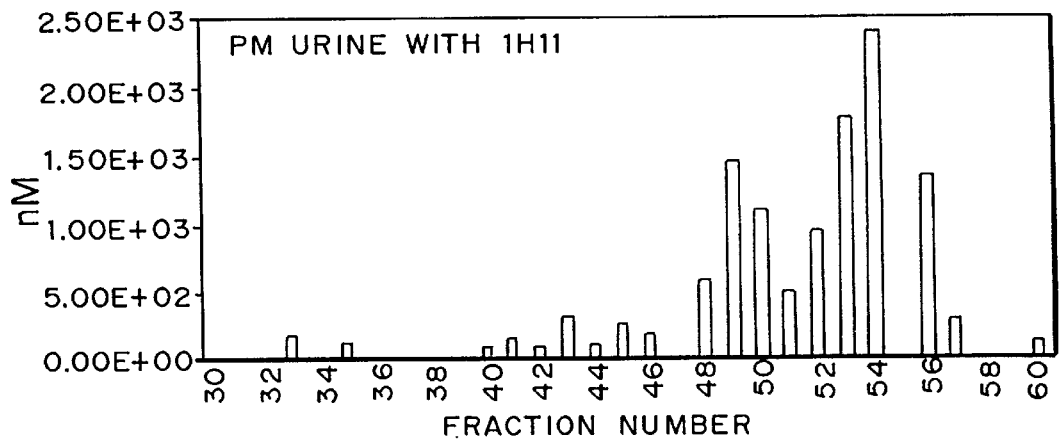
FIG. 1B
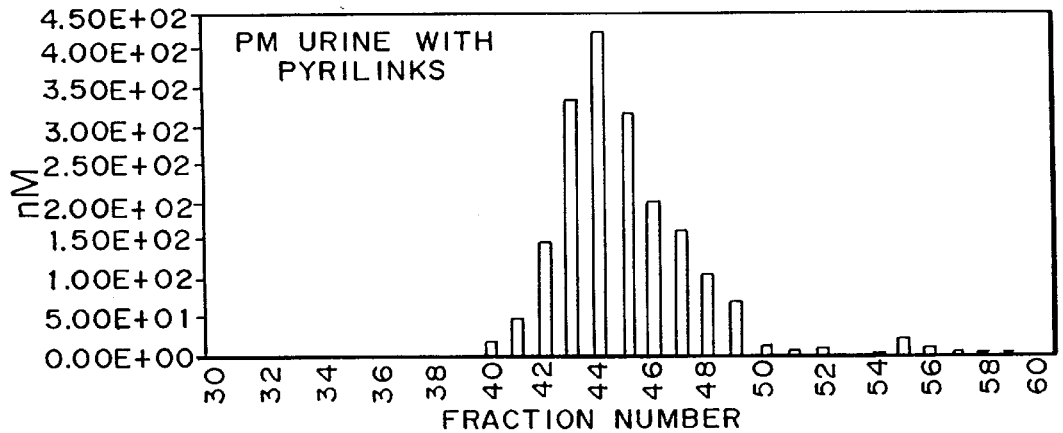
FIG. 1C

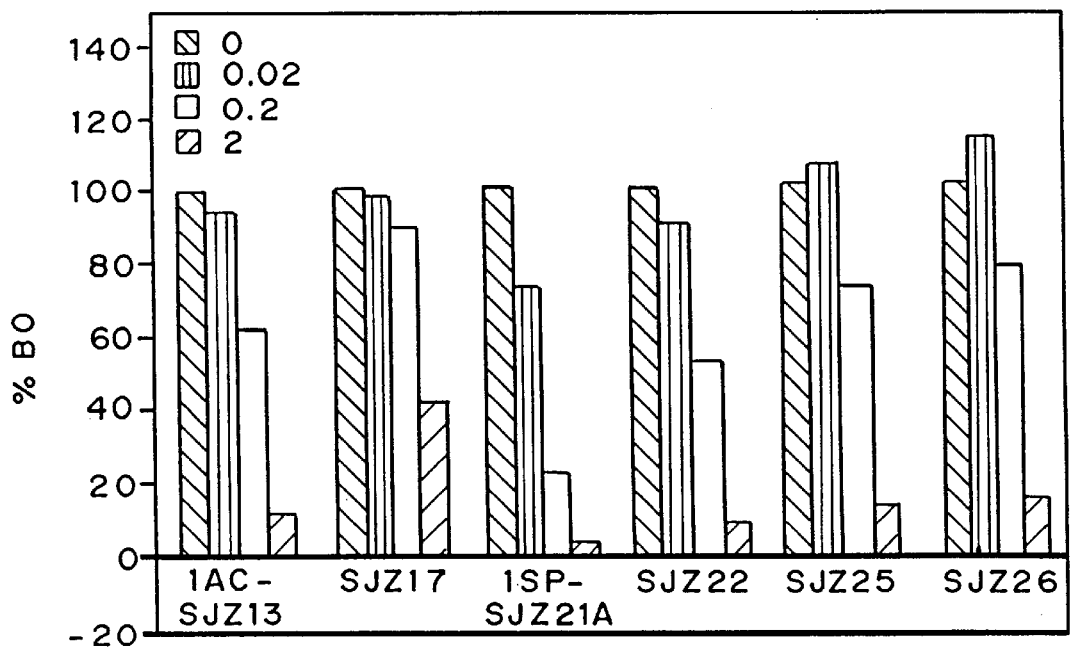
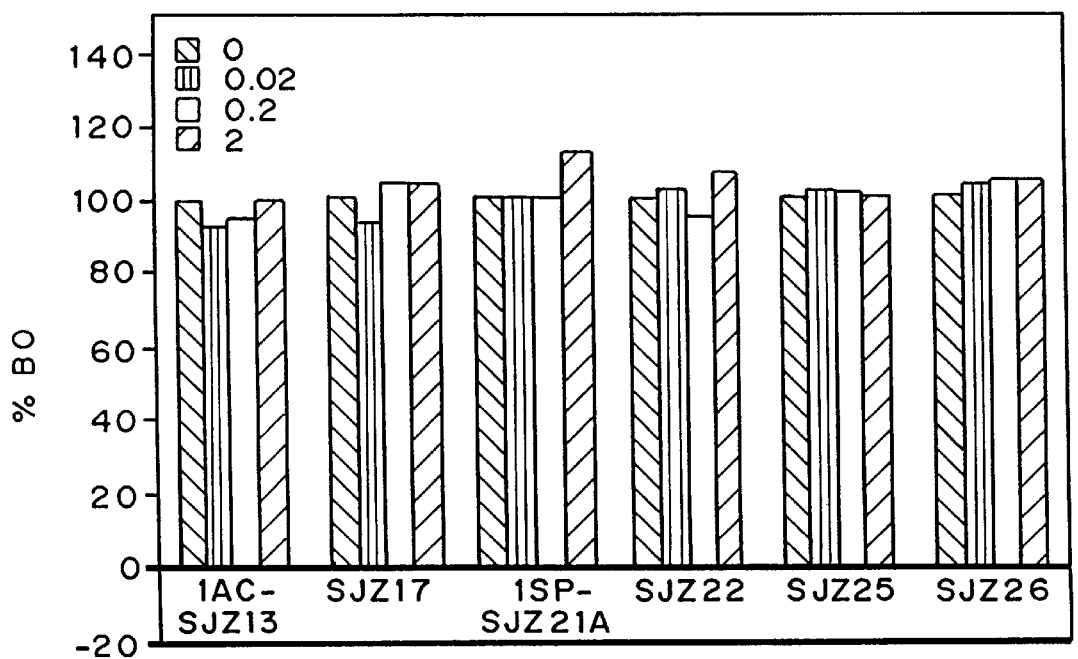

ANTIBODY TO AND ASSAY FOR PEPTIDE LINKED-PYRIDINOLINE AS INDICATOR OF BONE RESORPTION LEVEL

BACKGROUND OF THE INVENTION

The present invention is generally in the area of monoclonal antibodies useful in immunoassays, and in particular is a monoclonal antibody produced by a hybridoma deposited with the American Type Culture Collection, Rockville, Md. on Jan. 7, 1997, designated HB-12254, and a derivatized pyridinoline useful in immunoassays binding assays for peptide linked pyridinoline derived from naturally occurring bone collagen.

It is well established that antibodies are useful in immunoassays when the antibodies are directed against specific epitopes characteristic of a particular disease or metabolic condition. As described in U.S. Pat. No. 4,973,666 to Eyre, an antibody reactive with peptide sequence at the bone collagen hydroxypyridinium crosslinks in the amino-terminal of Type 1 Collagen in human urine can be used to correlate bone resorption, which is indicative of osteoporosis.

Osteoporosis is the most common bone disease in man. Primary osteoporosis, with increased susceptibility to fractures, results from a progressive net loss of skeletal bone mass. It is estimated to affect 15–20 million individuals in the United States. Its basis is an age-dependent imbalance in bone remodeling, i.e., in the rates of synthesis and resorption of bone tissue. About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., Science, 236,914 (1987)). Osteoporosis is most common in post-menopausal women who, on average, lose 15% of their bone mass in the 10 years after menopause. This disease also occurs in men as they get older and in young amenorrheic women athletes. Despite the major, and growing, social and economic consequences of osteoporosis, there are a limited number of methods available for measuring bone resorption rates in patients or normal subjects.

Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased. For this reason, urinary hydroxyproline has been used extensively as an amino acid marker for collagen degradation. Singer, F. R., et al. (1978) In: *Metabolic Bone Disease*, Vol. II (eds. Avioli, L. V. and Krane, S. M.) pp. 489–575, Academic Press, New York. A urinary, blood or saliva, assay for the whole-body output of degraded bone in 24 hours would be much more useful. Mineral studies (e.g., calcium balance) cannot do this reliably or easily.

The polymers of most generic types of vertebrate collagen require the formation of aldehyde-mediated cross-links for normal function. Collagen aldehydes are derived from a few specific lysine or hydroxylysine side-chains by the action of lysyl oxidase. Various di-, tri- and tetrafunctional cross-linking amino acids are formed by the spontaneous intra- and intermolecular reactions of these aldehydes within the newly formed collagen polymers; the type of cross-linking residue varies specifically with tissue type (see Eyre, D. R. et al. (1984) *Ann. Rev. Biochem.* 53: 717–748). Two basic pathways of cross-linking can be differentiated for the banded (67 nm repeat) fibrillar collagens, one based on lysine aldehydes, the other on hydroxylysine aldehydes. The lysine aldehyde pathway dominates in adult skin, cornea, sclera, and rat tail tendon and also frequently occurs in other soft connective tissues. The hydroxylysine aldehyde pathway dominates in bone, cartilage, ligament, most tendons and most internal connective tissues of the body, Eyre, D. R. et al. (1974) vide supra. The operating pathway is governed by whether lysine residues are hydroxylated in the telopeptide sites where aldehyde residues will later be formed by lysyl oxidase (Barnes, M. J. et al. (1974) *Biochem. J.* 139, 461). In both pathways and in most tissues the intermediate borohydride-reducible cross-linking residues disappear as the newly formed collagen matures, suggesting that they are relatively short-lived intermediates (Bailey, A. J. et al. (1971) *FEBS Lett.* 16, 86). Exceptions are bone and dentin, where the reducible residues persist in appreciable concentration throughout life, in part apparently because the rapid mineralization of the newly made collagen fibrils inhibits further spontaneous cross-linking interactions (Eyre, D. R. (1981) In: *The Chemistry and Biology of Mineralized Connective Tissues* (Veis, A. ed.) pp. 51–55, Elsevier, N.Y., and Walters, C. et al. (1983) *Calc. Tiss. Intl.* 35: 401–405).

Two chemical forms of 3-hydroxypyridinium cross-link have been identified. Both compounds are naturally fluorescent, with the same characteristic excitation and emission spectra (Fujimoto, D. et al. (1977) *Biochem. Biophys. Res. Commun.* 76, 1124, and Eyre, D. R. (1981) *Develop. Biochem.* 22, 50). These amino acids can be resolved and assayed directly in tissue hydrolysates with good sensitivity using reverse phase HPLC and fluorescence detection. (Eyre, D. R. et al. (1984) *Analyt. Biochem.* 137: 380–388).

In growing animals it has been reported that these mature cross-links may be concentrated more in an unmineralized fraction of bone collagen than in the mineralized collagen (Banes, A. J., et al. (1983) *Biochem. Biophys. Res. Commun.* 113, 1975). However, other studies on young bovine or adult human bone do not support this concept, (Eyre, D. R. (1985) In: *The Chemistry and Biology of Mineralized Tissues* (Butler, W. T. ed.) p. 105, Ebsco Media Inc., Birmingham, Ala.).

The presence of collagen hydroxypyridinium cross-links in human urine was first reported by Gunja-Smith and Boucek (Gunja-Smith, Z. and Boucek, R. J. (1981) *Biochem J.* 197: 759–762) using lengthy isolation procedures for peptides and conventional amino acid analysis. At that time, they were aware only of the hydroxylysyl pyridinoline form of the cross-link. Robins (Robins, S. P. (1982) *Biochem J.* 207: 617–620) has reported an enzyme-linked immunoassay to measure hydroxylysyl pyridinoline in urine, having raised polyclonal antibodies to this free amino acid conjugated to bovine serum albumin. This assay is intended to provide an index for monitoring increased joint destruction that occurs with arthritic diseases and is based, according to Robins, on the finding that pyridinoline is much more prevalent in cartilage than in bone collagen. In more recent work involving enzyme-linked immunoassay, Robins reports that lysyl pyridinoline is unreactive toward antiserum to hydroxylysyl pyridinoline covalently linked to bovine serum albumin (Robins et al. (1986) *Ann. Rheum. Diseases* 45, 969–973). Robins' urinary index for cartilage destruction is based on the discovery that hydroxylysyl pyridinoline, derived primarily from cartilage, is found in urine at concentrations proportional to the rate of joint cartilage resorption.

A method for determining the absolute rate of bone resorption by quantitating the concentration of peptide fragments attached to 3-hydroxypyridinium cross-links derived from bone collagen resorption in a body fluid is described by Eyre in U.S. Pat. No. 4,973,666. A preferred antibody for use in these assays is a monoclonal antibody referred to as 1H11, deposited with the American Type Culture Collection, Rockville, Md. under accession number HB10611, as described in U.S. Pat. No. 5,320,970 to Eyre and marketed by Ostex which antibody recognizes specific linear sequences occurring at cross linking sites.

Pyridinoline is a rigid ring structure. Pyridinoline exists in only two forms, hydroxy lysyl pyridinoline and lysyl pyridinoline, as opposed to the myriad of crosslinks and aging that affects the structure and conformation of adjacent peptide sequences. Much of the pyridinoline in urine is a byproduct of cartilage destruction, so that total pyridinoline is not a specific marker for bone resorption. Since pyridinoline is derived from many sources besides bone, it has limited specificity for detecting bone resorption and its reversal.

Other antibodies are being commercially marketed for use in diagnostic assays for osteoporosis, including antibodies marketed by Osteometer (Crosslaps™) and Metra Biosystems (Pyrilinks™) and Pyrilinks D™)). An antibody that could detect mature (as defined by presence of crosslinks) bone collagen fragments, eliminating the dependence on conformation of a peptide sequence, would greatly assist in use of bone specific crosslinker as a marker. Since 1H11 reacts with peptides linked through pyridinoline and not with pyridinoline itself or the linear peptide, i.e., recognition of the peptide is conformationally dependent, the immune reaction is expected to be influenced by factors influencing patient to patient peptide conformation, e.g., peptide sequence variation, isomeric differences in peptide due to crosslinking or other aging changes such as transversion, glycation which can affect conformation, as well as assay conditions affecting conformation.

The antibody marketed by Crosslaps reacts with a linear carboxy-terminal peptide from the alpha-1 chain of human type I collagen. The peptide alpha sequence is EKAHDGGR. This antibody is subject to much the same limitations as described for 1H11.

The Metra Pyrilinks 1 kit provides antibody that reacts with pyridinium crosslinks derived from collagen, including that from type I bone. Both crosslinks, pyridinoline (hydroxylysyl pyridinoline) and deoxypyridinoline (lysyl pyridinoline) are formed by enzyme lysyl oxidase. The Metra Pyrilinks D kit provides antibody that reacts with deoxypyridinoline which has been shown to be more specific to bone than hydroxypyridinoline.

These antibodies differ in their ability to differentiate peptides from different patient populations and body fluids.

It is an object of the present invention to provide a specific antibody for use in a diagnostic assay for osteoporosis using bodily fluids from postmenopausal (PM) women which correlates with bone loss.

It is another object of the present invention to provide pyridinoline analogs for use in immunoassays for pyridinoline.

SUMMARY OF THE INVENTION

Monoclonal antibodies, exemplified by Serex A93, have been developed that are immunoreactive with peptide linked pyridinoline and therefore can be used to quantitate cross linked peptides indicative of bone loss. The hybridoma producing the A93 antibody has been deposited with the American Type Culture Collection, Rockville, Md., under accession number HB-12254. The epitope recognized by the antibody is stable to acid hydrolysis stable and therefore is not a linear peptide. Studies further demonstrate that the pyridinoline is recognized when bound or when conjugated, but not in its free form found in urine. Studies demonstrate differences in immunoreactivity as compared to other commercially available antibodies immunoreactive with pyridinoline-containing peptides, as shown by FIGS. 1 and 2.

The antibody is useful in immunoassays predictive of osteoporosis, especially in determining bone loss in post-menopausal woman where the body fluid to be assayed is urine, blood or saliva. A93 has the advantage that its recognition of PLP is not dependent on conformation of a linear peptide but on a stable structure. Analogs of pyridinoline are disclosed which are useful with these antibodies or others in immunoassays.

BRIEF DESCRIPTION OF THE FIGURES

FIGS. 1a–1d are graphs of immunoreactivity of post-menopausal ("PM") urine, fractionated on a P-10 Biogel column, with four different antibodies: Serex A93 (FIG. 1a), 1H11 (FIG. 1b), Pyrilinks (FIG. 1c), and CrossLaps (FIG. 1d).

FIGS. 4a and 4b are graphs of the immunoreactivity of 1H11 (FIG. 4a) and 51A93 (FIG. 4b) with various non-pyridinoline containing peptide analogs of the NTx sequence QYDGKGVG: 1AC-SJZ13, SJZ17, 1SP-SJZ21A, SJZ22, SJZ22, SJZ25 and SJZ26.

DETAILED DESCRIPTION OF THE INVENTION

The invention described herein is an antibody which is reactive with peptide linked-pyridinoline generally, not restricted to specific collagen peptides, that can be used to quantify bone resorption as an indicator of osteoporosis. Although described with reference to a particular preferred antibody produced by a hybridoma deposited with the American Type Culture Collection, other antibodies reactive with the same or similar epitopes can be produced using known immunization conditions.

A hybridoma was deposited with the American Type Culture Collection, Rockville, Md., on Jan. 7, 1997, and designated HB 12254. The monoclonal antibody produced by this hybridoma is referred to herein as Serex 51A93. Serex and the inventors have contracted with the American Type Culture Collection, and agreed pursuant to 35 U.S.C. §112 and MPEP §608.01(p)(C), that:

(a) during the pendency of the application in the U.S. Patent and Trademark Office, access to the invention will be afforded to the Commissioner upon request;

(b) all restrictions upon availability to the public will be irrevocably removed upon granting of a U.S. patent;

(c) the deposit will be maintained in a public depository for a period of 30 years or 5 years after the last request of the deposit or for the effective life of the patent, whichever is longer; and (d) the deposit will be replaced if it should ever become not viable.

Characterization of Epitope Bound by 51A93

The following studies demonstrate the unique properties of this antibody. Four different studies were carried out using the Ostex antibody 1H11, as the comparison partner.

Reactivity with Fractionated Urine Fractions

The first study showed the similarity between the immunoreactivity of 51A93 and 1H11 with Biogel fractionated urine. Postmenopausal and preadolescent urine samples were fractionated on a Biogel P-10 column. Fractions from the column were pooled as follows:

| Postmenopausal Urine | | | Preadolescent Urine | | |
|---|---|---|---|---|---|
| Pools | Fractions | Volume (ml) | Pools | Fractions | Volume (ml) |
| 1A | 50–55 | 400–440 | 1 | 50–61 | 400–488 |
| 1B | 56–61 | 440–488 | 2 | 62–70 | 488–560 |
| 2 | 62–70 | 488–560 | | | |

It was found that both 51A93 and 1H11 reacted with the same fractions, as shown by FIGS. 1A and 1B and 2A and 2B, respectively. In contrast, antibodies obtained from Crosslaps (from Diagnostic Systems Laboratories, Inc., Webster, Tex.) and Metra Pyrilinks (from Metra Biosystems, Inc., Mountain View, Calif.) kits do not react with the 1H11 and 51A93 reactive fractions, as shown by comparison of FIGS. 1A and 1B and 2A and 2B with FIGS. 1C and 1D and 2C and 2D, respectively.

Reactivity with Peptide Containing Fractions

The second group of studies show the differences between 51A93 and 1H11 immunoreactivities.

Figure 1D:
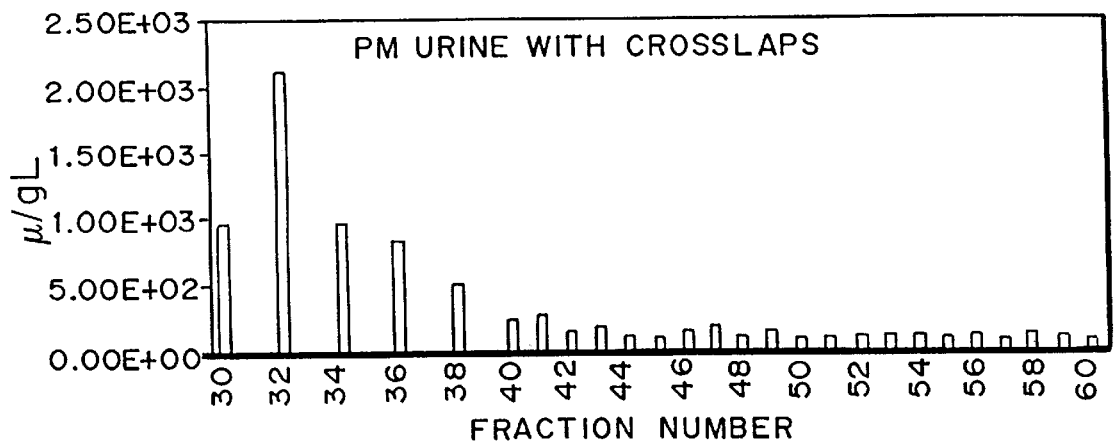
Figure 2A:
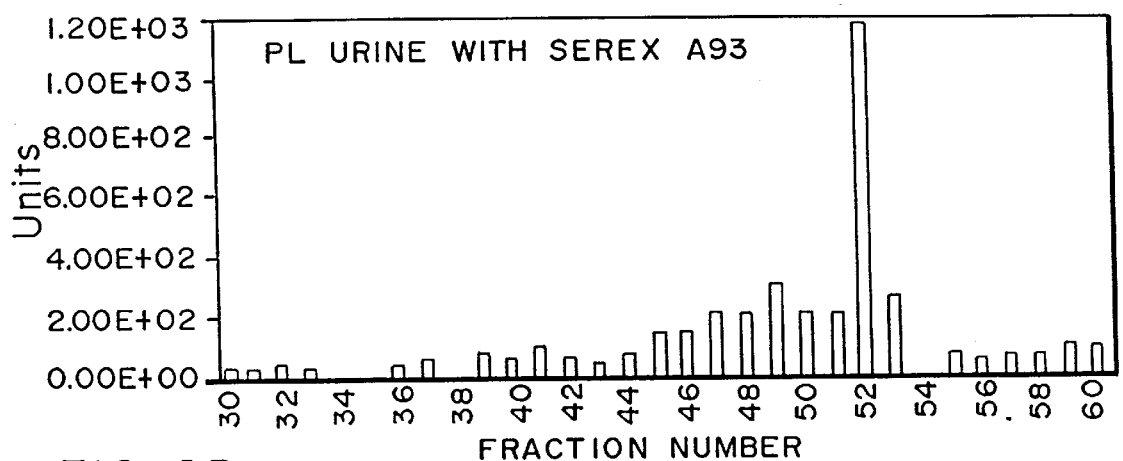
FIGS. 2a–2d are graphs of immunoreactivity of preadolescent ("PL") male urine, fractionated on a P-10 Biogel column, with four different antibodies: Serex A93 (FIG. 2a), 1H11 (FIG. 2b), Pyrilinks (FIG. 2c), and CrossLaps (FIG. 2d).
Figure 2B:
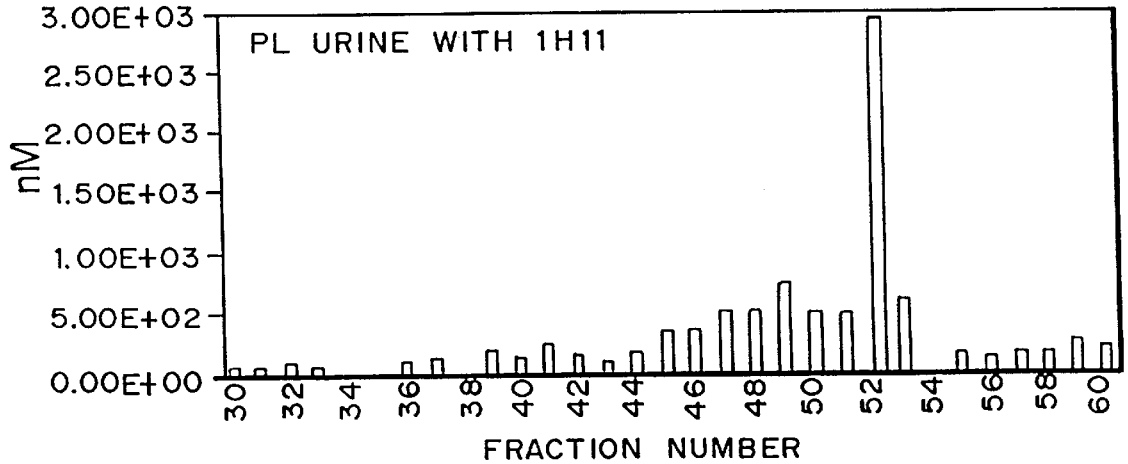
Figure 2C:
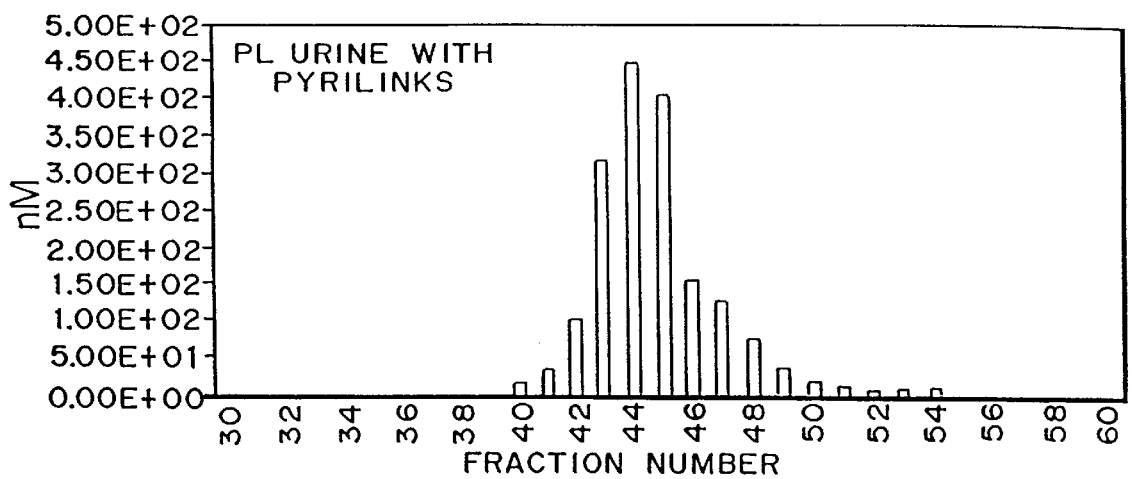
Figure 2D:
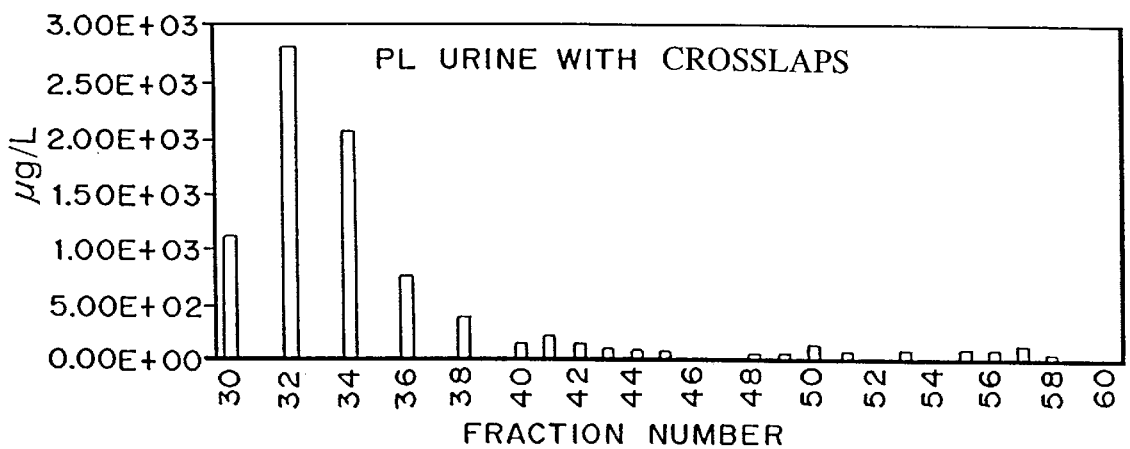
Figure 3A:
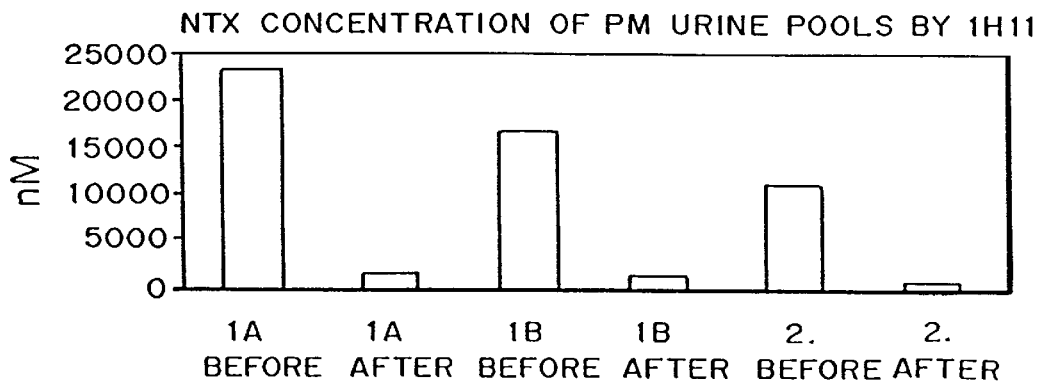
FIGS. 3a and 3b are comparisons of NTx or PLP concentration of PM urine pools assayed with: 1H11 (FIG. 3a) and Serex 51A93 (FIG. 3b).
Figure 3B:
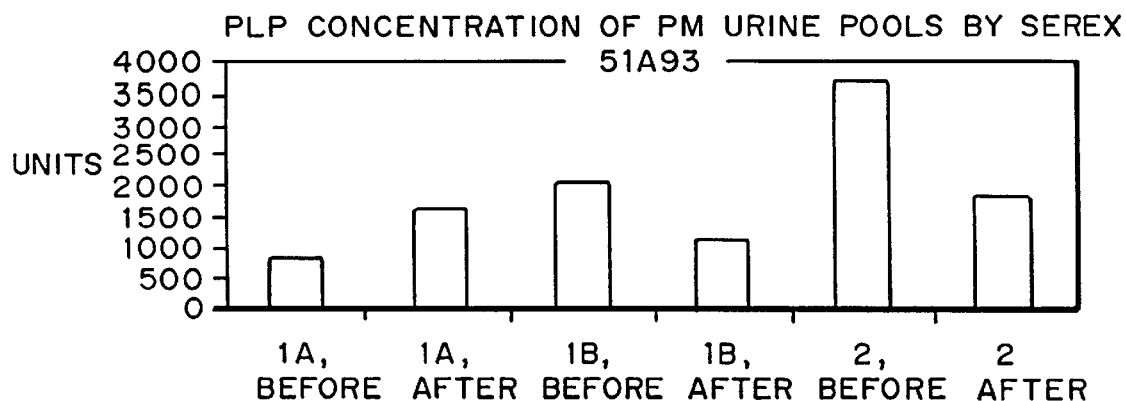
Figure 3C:
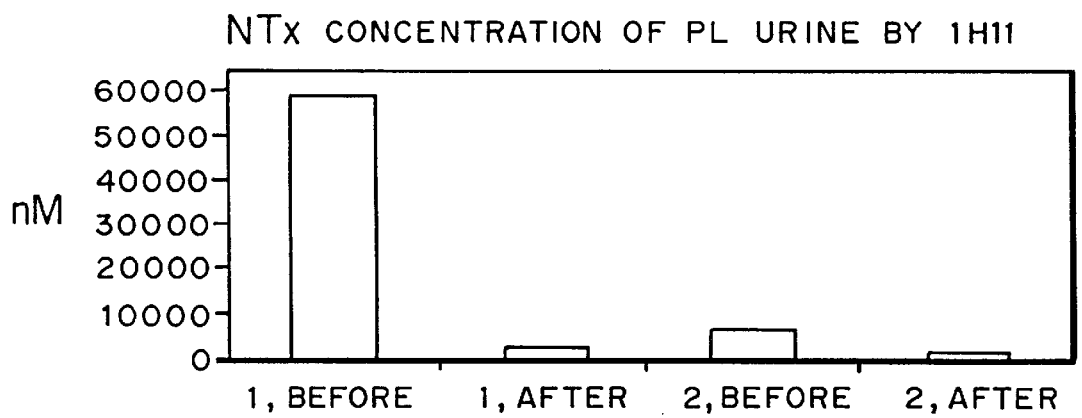
FIGS. 3c and 3d are comparisons of NTx or PLP concentration of PL urine pools assayed with: 1H11 (FIG. 3c) and Serex A93 (FIG. 3d).
Figure 3D:
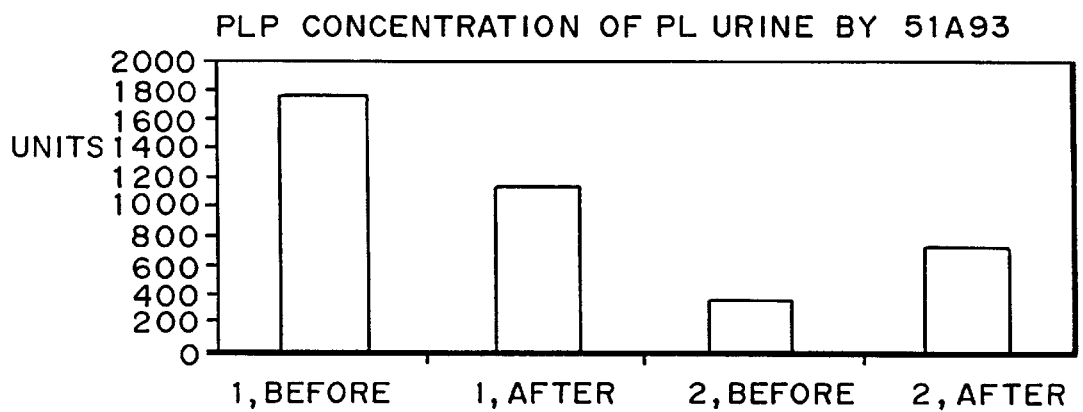

51A93 recognizes an epitope that is stable to acid hydrolysis since reactivity was conserved following hydrolysis, as shown by FIGS. 3B and 3d. In contrast, 1H11 loses all reactivity to the hydrolyzed sample, as shown by FIG. 3A and 3D, and Tables 1 and 2. This demonstrates that while 51A93 recognizes the same analytes as 1H11, the antibodies recognize very different epitopes, which suggests that the epitopes recognized by 51A93 is pyridinoline because the 51A93 epitope is acid hydrolysis stable while linear peptides are not.

Comparison of Immunoreactivities with Various Assay Calibrators

The immunoreactivities of 51A93 and 1H11 with the calibrators and ELISA plates in the Osteomark kit and Pyrilinks Metra kit were compared. Two studies were carried out using ELISA plate assays.

In the first study, BCE calibrators from the Osteomark Kit and free pyridinoline (Pyd) from Metra were tested at different concentrations to see if either of them inhibits 51A93. The results are shown in Table 3. Abbreviations are BCE, bone collagen equivalents; %Bo, percent bound at 0 concentration of analyte (as analyte in sample binds to antibody, the percent Bo decreases).

In the second study, plates from the Osteomark Kit and Pyrilinks Kit were used to see if 51A93 binds to them. The results are compiled in Table 4. 51A93 does not recognize the solid phase or the calibrators of the Ostex kit. Mab 51A93 is not inhibited by Ostex calibrators even at high levels but is slightly inhibited by pyridinoline, as demonstrated in Table 3. In addition, 51A93 strongly recognizes Pyrilinks plates but does not recognize Ostex plates. It appears that 51A93 recognizes pyridinoline in bound form.

These results clearly demonstrate that 51A93 is different from 1H11.

Comparison of Immunoreactivities with Peptides

The immunoreactivity of 1H11 and Serex 51 A93 with different synthetic peptide analogs of the NTx sequences were analyzed in ELISA plate assays. Aliquots of peptides at three different concentrations were added to the assay to determine the effect on antibody binding.

The results were compiled in Table 5 and graphed in FIGS. 4A and 4B. These results further differentiate 51A93 from 1H11. 1H11 was inhibited by all of the peptides tested while 51A93 was not.

51A93 strongly recognizes the Metra solid phase, indicating that it recognizes pyridinoline when conjugated. 51A93 does not recognize the Metra pyridinoline calibrators, nor does it recognize the free pyridinoline in Biogel fractions. The conclusion is that 51A93 recognizes pyridinoline in its bound but not free state; therefore 51A93 recognizes pyridinoline in any crosslinked fragments but not telopeptide fragments like 1H11.

51A93 does not recognize peptide; 1H11 recognizes free peptide. The last study compared the immunoreactivity of 51A93 and 1H11 with different peptides, as shown in FIG. 4 and Table 5. This study clearly shows the dependency of 1H11 on the peptide epitopes, in contrast to 51A93 which is not dependent on a peptide epitopes.

Immunoassays

The 51A93 antibody (also referred to as A93 antibody) is useful in immunoassays for quantification of bone resorption from a variety of body fluids, especially blood and blood components and urine. Preferred assays are immunoassays of urine, blood and saliva, and more preferably solid phase immunoassays, where the antibody or its analyte may be immobilized to a solid support. In some embodiments, the antibody is labelled with a detectable label such as a radiolabel, fluorescent or enzyme label, or colloidal gold or dye label, all of which are known to those skilled in the art. Accordingly, the antibody may be provided alone, labelled, or as part of an immunoassay kit, including other reagents required for the immunoassay, such as a solid support, detectable labels, or competitive ligands.

Pyridinoline Analogs

Ligands useful in the assay for PLP will have association constants ranging from $10^3$ to $10^{12}$ M$^{-1}$. These can be analyte, i.e., collagen or bone peptides including crosslinked or conjugated pyridinoline and pyridinium analogs or a derivatized molecule of such preferred ligands are crosslinked or conjugated to protein or peptide carriers. As described herein, a preferred pyridinoline analog has the following general formula:

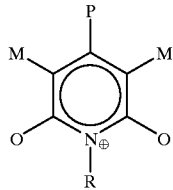

wherein:

R is selected from the group consisting of alkyl, $C_{1-20}$ straight, branched or cyclic alkenyl, $C_{2-20}$ straight or branched alkyne, $C_{8-20}$ cyclic alkyne, aralkyl, and alkaryl, wherein alkyl includes $C_{1-20}$ straight, branched or cyclic alkyl groups, and wherein positions 3 or more carbons away from the ring can include substituents selected from the group consisting of —OH, —SH, —O-alkyl, —S-alkyl, —NH$_2$, —NHalkyl, —NHacyl including amino acids and peptide residues, —N(alkyl)$_2$, —CO$_2$H, —CO$_2$-alkyl, —SO$_3$H, —PO$_3$H, O is selected from the group consisting of H and methyl, M and P are independently selected from the group consisting of H, alkyl, $C_{2-20}$ straight, branched or cyclic alkenyl, $C_{2-20}$ straight or branched alkyne, $C_{8-20}$ cyclic alkyne, aralkyl, alkaryl, one or more amino acids, wherein alkyl includes $C_{1-10}$ straight, branched or cyclic alkyl groups, and wherein positions 3 or more carbons away from the ring can include substituents selected from the group consisting of —OH, —SH, —O-alkyl, —S-alkyl, —NH$_2$, —NHalkyl, —NHAcyl, —N(alkyl)$_2$, —CO$_2$H, —CO$_2$-alkyl, —SO$_3$H, —PO$_3$H, including amino acids and peptides.

The term alkyl refers to a $C_1$ to $C_{20}$ straight, branched or cyclic alkyl substituent.

The term aralkyl refers to an aryl group with an alkyl substituent.

The term alkaryl refers to an alkyl group that has an aryl substituent.

The term alkene, as referred to herein, and unless otherwise specified, refers to a straight, branched or cyclic alkene group of $C_2$ to $C_{20}$, and specifically includes vinyl and allyl.

The term alkyne, as referred to herein, and unless otherwise specified, refers to a straight, or branched alkyne group of $C_2$ to $C_{20}$ or a cyclic alkyne group of $C_8$ to $C_{20}$.

The present invention will be further understood by reference to the following non-limiting example.

Example 1
Immunoassay Using Serex Monoclonal Antibody.
Gold-Anti PLP Antibody Conjugate Preparation Colloidal gold, prepared according to Roth J. in Techniques in Immunocytochemistry, Vol. 1, p.110 ed. by Bullock, G. and Petrusz, P., Academic Press, Inc. 1982, was conjugated first to goat anti-mouse IgG, Fc antibody from Jackson ImmunoResearch Lab, In. (West Grove, Pa.) according to procedure described by Roth J. in Techniques in Immunocytochemistry, Vol. 2, p. 230 ed. by Bullock, G. and Petrusz, P., Academic Press, Inc. 1982. 200 μg of purified antibody was conjugated to 10 ml of 0.01% colloidal gold in 2.5 mM borate buffer, pH 9.0. After blocking by bringing to 0.1% bovine serum albumin, the preparation was centrifuged the supernatant with unbound antibody was discarded and the particles were resuspended in 1 ml of diluent consisting of 0.025 M Tris/HCl buffer, pH 8.2, 0.1% bovine serum albumin and 0.05% sodium azide.

1 ml of concentrated gold anti-mouse 1gG, Fc conjugate was interacted with 1 ml of monoclonal anti-peptide linked pyridinoline (PLP) antibody 93A (ATCC Hb-12254) at concentration 0.1 mg/ml in a buffer consisting of 0.025 M Tris/HC1 buffer, pH 8.2, 0.1% bovine serum albumin, and 0.05% sodium azide. After 1 hour of interaction at room temperature, the gold particles were centrifuged; supernatant with unbound was discarded and the particles were resuspended in 1 ml of diluent consisting of 0.025 M Tris/HC1 buffer, pH 8.2, 0.1% bovine serum albumin, and 0.05% sodium azide.

100 μl of final preparation of gold conjugate was placed in a microtiter plate well and O.D. at 550 nm was read. The working solution of gold conjugate had an O.D. of 2.332 at 550 nm.

The Membrane

Nitrocellulose (Millipore STHF040000) was cut into a square piece 10 cm by 10 cm. Using a CAMAG instrument, a first trap (trap for unbound material) was laid down on the membrane in a form of band 3 mm wide approximately 2.5 cm from the bottom of the membrane. Forty μl of the coating solution was used to make the band. The trap material was 1-methyl-5-(3-(1-(5"-carboxypentyl))pyridinium)-2-pyrrolidinone bromide conjugated to bovine serum albumin by the carbodiimide method. The concentration of coating conjugate was 0.5 mg/ml of 0.05 M phosphate buffer, pH 7.5. The second trap (trap for bound material) was laid down in the form of a 3 mm wide band 2 mm distal to the first trap. Forty μl of the coating solution was used to make the band. The trap material was goat anti-mouse IgG, Fc antibody from Jackson ImmunoResearch (West Grove, Pa.) used at concentration 0.5 mg/ml in 0.05 M phosphate buffer, pH 7.5.

After deposition of the traps, the membrane was dried for several hours at room temperature and then soaked for 30 minutes in a blocking buffer consisting of 0.5% casein (Hammarsten), 0.25 mM trans-1,2 diaminocyclohexane-N, N,N$^1$,N$^1$-tetraacetic acid (CDTA) at pH 7.5. Finally, the membrane is dried in a drying oven at 29° C. for 1 hour. The dried membrane was cut into individual strips, 4 mm wide.

Assay Run

Individual strips were placed into small test tubes containing 100 μl urine samples of known BCE value (BCE units are from the Ostex Assay) and 10 μl of gold conjugate and chromatographed.

Visual Test Results

For PLP negative sample, most of the color appeared at the first trap of the strip and only minimal amount of color at the second trap site. With increasing amounts of BCE, the color of the second trap appeared gradually darker reaching the same intensity as the first trap at the level of 769 nM BCE. At higher levels of BCE the color of the first trap appeared lighter than the color of the second trap.

Measurement of Test Results

Figure 5:
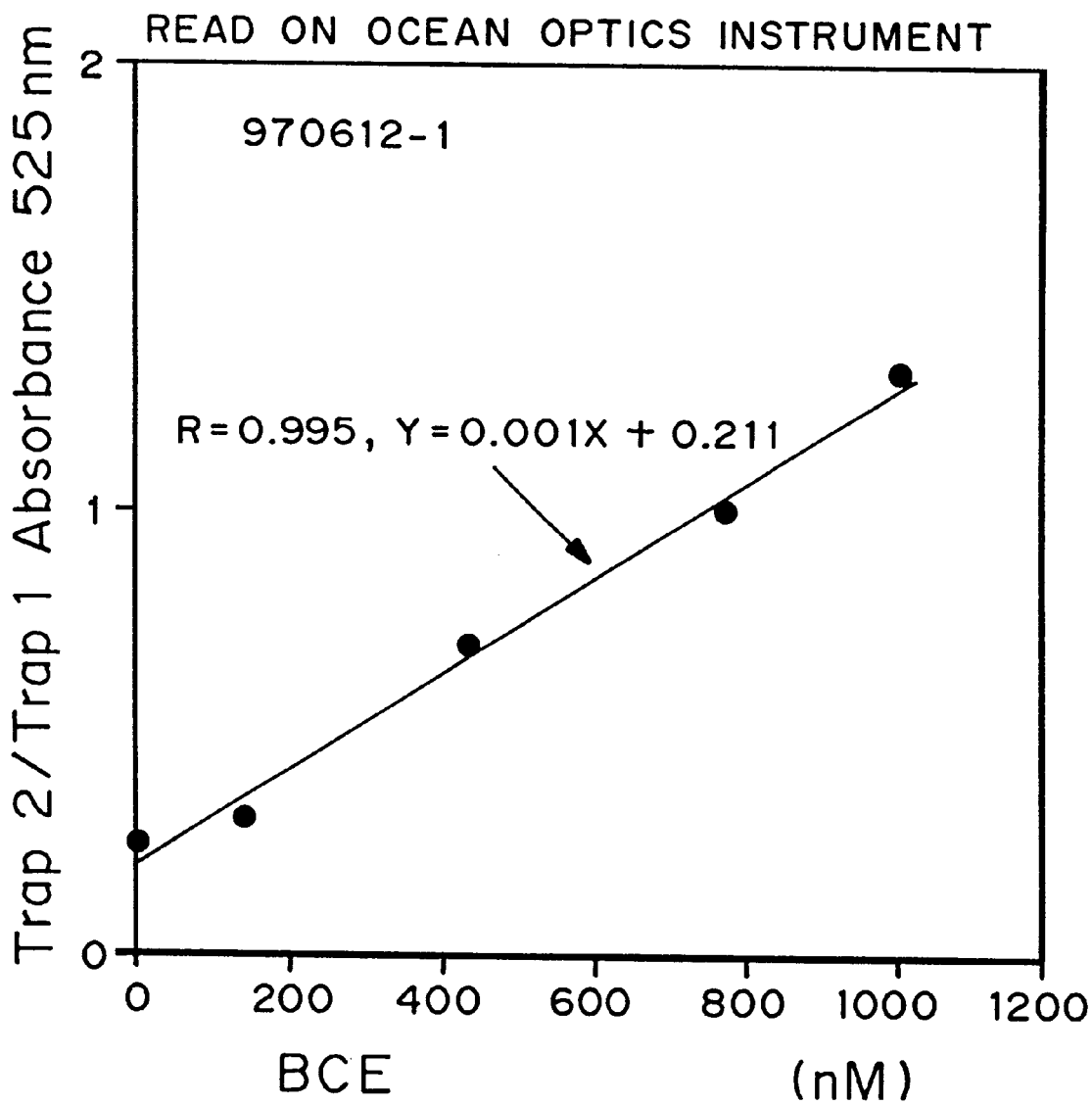
FIG. 5 is a graph of the results of the osteoporosis assay, read on reflectometer (Ocean Optics, Inc. Dunedin, Fla.), plotting trap 2/trap 1 absorbance at 525 nm versus PLP concentration (nM).

The absorbance at 525 nm for each trap was measured by diode ray spectrophotometer (from Ocean Optics, Dunedin, Fla.). The results are summarized below and shown in FIG. 5:

Results Obtained with Osteoporosis Dipsticks

| PLP Level nM/L | Trap 1 Band* | Trap 2 Band* | Ratio Trap 1/Trap 2 |
|---|---|---|---|
| 0 | 0.345 | 0.088 | 0.25 |
| 141 | 0.377 | 0.116 | 0.31 |
| 436 | 0.372 | 0.257 | 0.69 |
| 769 | 0.403 | 0.399 | 0.99 |
| 1000 | 0.328 | 0.426 | 1.30 |

*The values are the mean of readings of two strips

TABLE 1

Postmenopausal Urine Pools

|  | 1H11 (nM) | Serex 51A93 (units) |
|---|---|---|
| Pool 1A, Before Hydrolysis | 23,240 | 876 |
| Pool 1A, After Hydrolysis | 1,295 | 1,677 |
| Pool 1B, Before Hydrolysis | 17,018 | 2,097 |
| Pool 1B, After Hydrolysis | 982 | 1,088 |
| Pool 2, Before Hydrolysis | 10,853 | 3,690 |
| Pool 2, After Hydrolysis | 508 | 1,814 |

TABLE 2

Preadolescent Urine Pools

|  | 1H11 (nM) | Serex 51A93 (units) |
|---|---|---|
| Pool 1, Before Hydrolysis | 59,256 | 1,767 |
| Pool 1, After Hydrolysis | 1,287 | 1,130 |
| Pool 2, Before Hydrolysis | 5,838 | 352 |
| Pool 2, After Hydrolysis | 810 | 709 |

TABLE 3

Inhibition Studies of Serex 51A93 by Calibrators

| Bone Collagen Equivalents (nM) | A 450 | % B0 | Pyd (mg/ml) | A 450 | % B0 |
|---|---|---|---|---|---|
| 0 | 1,686 | 100 | 0 | 1,496 | 100 |
| 30 | 1,676 | 99 | 0.001 | 1,302 | 87 |
| 100 | 1,777 | 105 | 0.01 | 1,275 | 85 |
| 300 | 1,730 | 103 | 0.1 | 1,327 | 89 |
| 600 | 1,695 | 101 | 1 | 1,249 | 83 |
| 1,000 | 1,747 | 104 |  |  |  |
| 3,000 | 1,787 | 106 |  |  |  |

TABLE 4

Binding Studies of Serex 51A93 on Pyrilinks and Osteomark Plates

| Plates | Titers | A450 |
|---|---|---|
| Pyrilinks | 1:30 k | 2,567 |
| Pyrilinks | 1:10 k | 2,827 |
| Osteomark | 1:1 k | 0.149 |
| Osteomark | 1:5 k | 0.048 |
| Osteomark | 1:10 k | 0.039 |
| Osteomark | 1:30 k | 0.013 |

TABLE 5

Inhibitition Studies by Peptides

| Peptides | Concentration (mg/mL) | 1H11 A450 | 1H11 % B0 | Serex 51A93 A450 | Serex 51A93 % B0 |
|---|---|---|---|---|---|
| 1AC-SJZ13 | 0 | 989 | 100 | 625 | 100 |
|  | 0.02 | 934 | 94 | 580 | 93 |
|  | 0.2 | 612 | 62 | 592 | 95 |
|  | 2 | 112 | 11 | 629 | 100 |
| SJZ17 | 0 | 989 | 100 | 625 | 100 |
|  | 0.02 | 966 | 98 | 590 | 94 |
|  | 0.2 | 879 | 89 | 650 | 104 |
|  | 2 | 407 | 41 | 649 | 104 |
| 1SP-SJZ21A | 0 | 989 | 100 | 625 | 100 |
|  | 0.02 | 726 | 73 | 627 | 100 |
|  | 0.2 | 213 | 22 | 623 | 100 |
|  | 2 | 27 | 3 | 701 | 112 |
| SJZ22 | 0 | 989 | 100 | 105 | 100 |
|  | 0.02 | 878 | 89 | 637 | 102 |
|  | 0.2 | 518 | 52 | 594 | 95 |
|  | 2 | 81 | 8 | 666 | 107 |
| SJZ25 | 0 | 1,099 | 100 | 1,763 | 100 |
|  | 0.02 | 1,170 | 106 | 1,790 | 102 |
|  | 0.2 | 790 | 72 | 1,780 | 101 |
|  | 2 | 127 | 12 | 1,762 | 100 |
| SJZ26 | 0 | 1,099 | 100 | 1,763 | 100 |
|  | 0.02 | 1,240 | 113 | 1,820 | 103 |
|  | 0.2 | 850 | 74 | 1,830 | 104 |
|  | 2 | 152 | 14 | 1,839 | 104 |

We claim:

1. An antibody reactive with the pyridinoline in peptide-linked-pyridinoline and not free pyridinoline which is useful in an assay to indicate bone resporption.

2. The antibody of claim 1 produced by a hybridoma deposited with the American Type Culture Collection, Rockville, Md., designated HB 12254.

3. The antibody of claim 1 further comprising a label for detection in an immunoassay.

4. The antibody of claim 1 immobilized or conjugated to a substrate or solid phase for use in an immunoassay.

5. A hybridoma deposited with the American Type Culture Collection, Rockville, Md., designated HB 12254.

6. A kit for a biological sample to quantify bone resorption comprising:

an antibody reactive with the pyridinoline in peptide-linked-pyridinoline and not free pyridinoline which is useful in an assay to correlate bone resorption.

7. The kit of claim 6 further comprising a ligand or binding partner selected from the group consisting of bone or collagen fragments containing pyridinoline or pyridine analogs having an affinity between $10^3$ $M^{-1}$ and $10^{12}$ $M^{-1}$, wherein binding of peptide linked pyridinoline in the sample inhibits binding of the ligands to the antibody.

8. The kit of claim 6 further comprising a solid support to which the antibody is bound.

9. The kit of claim 7 wherein the antibody or the binding partner is labelled with a detectable label.

10. The kit of claim 6 comprising monoclonal antibody produced by a hybridoma deposited with the American Type Culture Collection, Rockville, Md., designated HB 12254.

11. The kit of claim 7 wherein the pyridinoline analog is a pyridine derivative of the following general formula:

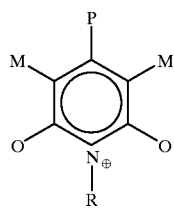

wherein:
- R is selected from the group consisting of alkyl, $C_{1-20}$ straight, branched or cyclic alkenyl, $C_{2-20}$ straight or branched alkyne, $C_{8-20}$ cyclic alkyne, aralkyl, and alkaryl,
- wherein alkyl includes $C_{1-20}$ straight, branched or cyclic alkyl groups, and
- wherein positions 3 or more carbons away from the ring can include substituents selected from the group consisting of —OH, —SH, —O-alkyl, —S-alkyl, —$NH_2$, —NHalkyl, —NHAcyl, NHamino acid and NHpeptide, —$N(alkyl)_2$, —$CO_2H$, —$CO_2$-alkyl, —$SO_3H$, —$PO_3H$,
- O is selected from the group consisting of H and methyl,
- M and P are independently selected from the group consisting of H, alkyl, $C_{2-20}$ straight, branched or cyclic alkenyl, $C_{2-20}$ straight or branched alkyne, $C_{8-20}$ cyclic alkyne, aralkyl, alkaryl, amino acids, and peptides,
- wherein alkyl includes $C_{1-20}$ straight, branched or cyclic alkyl groups, and
- wherein positions 3 or more carbons away from the ring can include substituents selected from the group consisting of —OH, —SH, —O-alkyl, —S-alkyl, —$NH_2$, —NHalkyl, —$N(alkyl)_2$, —$CO_2H$, —$CO_2$-alkyl, —$SO_3H$, and —$PO_3H$.

12. A method for determining bone resorption comprising
obtaining a sample of urine, blood, saliva or other bodily fluid from a patient,
reacting the sample with an antibody reactive with the pyridinoline in a peptide-linked-pyridinoline and not free pyridinoline which is useful in an assay to determine bone resorption, and
correlating the extent of the reaction with calibrators to determine the amount of bone resorption.

13. The method of claim 12 further comprising reacting with the patient sample and antibody a binding partner selected from the group consisting of bone or collagen fragments, pyridinoline, or pyridine analogs, wherein the binding partner inhibits the binding of the peptide-linked pyridinoline in the sample to the antibody.

14. The method of claim 13 wherein the antibody or binding partner is bound to a solid support further comprising applying the patient sample to the solid support to which the antibody or binding partner is bound.

15. The method of claim 12 wherein the antibody is a monoclonal antibody produced by a hybridoma deposited with the American Type Culture Collection, Rockville, Md., designated HB 12254.

16. The method of claim 13 wherein the pyridinoline analog is a pyridine derivative and has the following general formula:

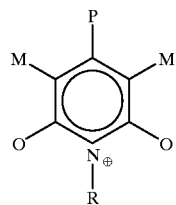

wherein:
- R is selected from the group consisting of alkyl, $C_{1-20}$ straight, branched or cyclic alkenyl, $C_{2-20}$ straight or branched alkyne, $C_{8-20}$ cyclic alkyne, aralkyl, and alkaryl,
- wherein alkyl includes $C_{1-20}$ straight, branched or cyclic alkyl groups, and
- wherein positions 3 or more carbons away from the ring can include substituents selected from the group consisting of —OH, —SH, —O-alkyl, —S-alkyl, —$NH_2$, —NHalkyl, NHAcyl amino acids and peptides, —$N(alkyl)_2$, —$CO_2H$, —$CO_2$-alkyl, —$SO_3H$, —$PO_3H$,
- O is selected from the group consisting of H and methyl,
- M and P are independently selected from the group consisting of H, alkyl, $C_{2-20}$ straight, branched or cyclic alkenyl, $C_{2-20}$ straight or branched alkyne, $C_{8-20}$ cyclic alkyne, aralkyl, alkaryl, amino acids and peptides,
- wherein alkyl includes $C_{1-20}$ straight, branched or cyclic alkyl groups, and
- wherein positions 3 or more carbons away from the ring can include substituents selected from the group consisting of —OH, —SH, —O-alkyl, —S-alkyl, —$NH_2$, —NHalkyl, —NHAcyl, NHamino acid and NHpeptide, —$N(alkyl)_2$, —$CO_2H$, —$CO_2$-alkyl, —$SO_3H$, and —$PO_3H$.

* * * * *